(12) United States Patent
Trieu et al.

(10) Patent No.: US 8,632,524 B2
(45) Date of Patent: Jan. 21, 2014

(54) INJECTABLE BIOCOMPATIBLE MATERIAL DELIVERY SYSTEM

(75) Inventors: Hai H. Trieu, Cordova, TN (US); Jeff R. Justis, Germantown, TN (US); Michael C. Sherman, Memphis, TN (US); Dimitri K. Protopsaltis, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1770 days.

(21) Appl. No.: 11/471,993

(22) Filed: Jun. 21, 2006

(65) Prior Publication Data

US 2007/0299426 A1 Dec. 27, 2007

(51) Int. Cl.
*A61K 9/22* (2006.01)
*A61F 2/28* (2006.01)

(52) U.S. Cl.
USPC ....... 604/890.1; 604/21; 604/264; 623/23.61; 623/23.62

(58) Field of Classification Search
USPC ............. 604/19–21, 113–114, 191, 186–187, 604/235, 624, 506, 890.1; 606/92–94; 623/23.61, 23.62
See application file for complete search history.

(56) References Cited

U.S. PATENT DOCUMENTS

| 5,195,526 | A | * | 3/1993 | Michelson | 600/431 |
|---|---|---|---|---|---|
| 6,264,659 | B1 | * | 7/2001 | Ross et al. | 606/93 |
| 6,676,664 | B1 | * | 1/2004 | Al-Assir | 606/94 |
| 7,371,241 | B2 | * | 5/2008 | Evans et al. | 606/92 |
| 7,720,533 | B2 | * | 5/2010 | Behravesh et al. | 604/20 |
| 8,123,756 | B2 | * | 2/2012 | Miller et al. | 606/92 |
| 2005/0209601 | A1 | | 9/2005 | Bowman et al. | |
| 2005/0209602 | A1 | | 9/2005 | Bowman et al. | |
| 2005/0270897 | A1 | * | 12/2005 | McCoy | 366/130 |
| 2006/0142703 | A1 | * | 6/2006 | Carter et al. | 604/264 |
| 2006/0264965 | A1 | * | 11/2006 | Shadduck et al. | 606/92 |
| 2007/0100449 | A1 | * | 5/2007 | O'Neil et al. | 623/13.14 |
| 2007/0150063 | A1 | * | 6/2007 | Ruberte et al. | 623/17.16 |
| 2008/0200916 | A1 | * | 8/2008 | Murphy | 606/94 |
| 2008/0234625 | A1 | * | 9/2008 | Dacquay et al. | 604/19 |

* cited by examiner

*Primary Examiner* — Quynh-Nhu H Vu
(74) *Attorney, Agent, or Firm* — Sorell Lenna & Schmidt LLP (57) ABSTRACT

An injectable biocompatible material delivery system is disclosed and can include an injector and a material delivery cannula that can be in fluid communication with the injector. Further, the injectable biocompatible material delivery system can include a light source that can be configured to emit light to at least a portion of the injector, at least a portion of the material delivery cannula, or a combination thereof. Further, the light source can be configured to activate an injectable biocompatible material as it moves through the system.

20 Claims, 10 Drawing Sheets

INJECTABLE BIOCOMPATIBLE MATERIAL DELIVERY SYSTEM

FIELD OF THE DISCLOSURE

The present disclosure relates generally to orthopedics and orthopedic surgery. More specifically, the present disclosure relates to the delivery of injectable biocompatible materials for treating, repairing, or augmenting bone and other tissue.

BACKGROUND

In human anatomy, the spine is a generally flexible column that can take tensile and compressive loads. The spine also allows bending motion and provides a place of attachment for ribs, muscles and ligaments. Generally, the spine is divided into three sections: the cervical spine, the thoracic spine and the lumbar spine. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column may be subjected. At the same time, the intervertebral discs can allow adjacent vertebral bodies to move relative to each other a limited amount, particularly during bending, or flexure, of the spine. Thus, the intervertebral discs are under constant muscular and/or gravitational pressure and generally, the intervertebral discs are the first parts of the lumbar spine to show signs of deterioration.

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

In order to treat facet joint degeneration or disc degeneration, it can be desirable to inject a biocompatible material into or around the facet joint or disc. After the biocompatible material is injected a surgeon must allow the material to cure in situ or force the material to cure in situ, e.g., apply a curing energy to the material. Accordingly, in order to reduce surgery time it may be beneficial to reduce the in situ curing time of the injected biocompatible material.

DETAILED DESCRIPTION OF THE DRAWINGS

An injectable biocompatible material delivery system is disclosed and can include an injector and a material delivery cannula that can be in fluid communication with the injector. Further, the injectable biocompatible material delivery system can include a light source that can be configured to emit light to at least a portion of the injector, at least a portion of the material delivery cannula, or a combination thereof. Further, the light source can be configured to activate an injectable biocompatible material as it moves through the system.

In another embodiment, an injectable biocompatible material delivery system is disclosed and can include an injector and a material delivery cannula in fluid communication with the injector. A material delivery channel can be established within the injector and the material delivery cannula. Moreover, the system can include an energy source that can be configured to emit curing energy to at least a portion of the material delivery channel. Also, the energy source can be configured to activate an injectable biocompatible material as it moves through the material delivery channel.

In yet another embodiment, an injectable biocompatible material delivery system is disclosed and can include a syringe. A material delivery cannula can be coupled to the syringe and a material delivery trocar can be coupled to the material delivery cannula. Additionally, a material delivery channel can be established within the syringe, the material delivery cannula, and the material delivery trocar. The system can also include an energy source that can be configured to emit curing energy to at least a portion of the material delivery channel. Further, the energy source can be configured to activate an injectable biocompatible material as it moves through the material delivery channel.

In still another embodiment, a syringe is disclosed and can include a barrel that can have a proximal end and a distal end. The syringe can also include a plunger that can be slidably disposed within the barrel. Moreover, the syringe can include a curing head that can circumscribe the distal end of the barrel. The curing head can be configured to transmit curing energy into an injectable biocompatible material as the injectable biocompatible material passes through the distal end of the barrel.

In yet still another embodiment, a material delivery cannula is disclosed and can include a proximal end and a distal end. A curing head can circumscribe the proximal end of the material delivery cannula. Further, the curing head can be configured to transmit curing energy into an injectable biocompatible material as the injectable biocompatible material passes through the proximal end of the material delivery cannula.

In another embodiment, a material delivery cannula is disclosed and can include a proximal end and a distal end. A curing head can circumscribe the distal end of the material delivery cannula. Further, the curing head can be configured to transmit curing energy into an injectable biocompatible material as the injectable biocompatible material passes through the distal end of the material delivery cannula.

In yet another embodiment, a material delivery trocar is disclosed and can include a proximal end and a distal end. A curing head can circumscribe the proximal end of the material delivery trocar. The curing head can be configured to transmit curing energy into an injectable biocompatible material as the injectable biocompatible material passes through the proximal end of the material delivery trocar.

In still yet another embodiment, a method of treating a patient is disclosed. The method can include pressurizing the injectable biocompatible material within a material delivery system and activating the injectable biocompatible material while the injectable biocompatible material moves through the system.

Description of Relevant Anatomy

Figure 1:
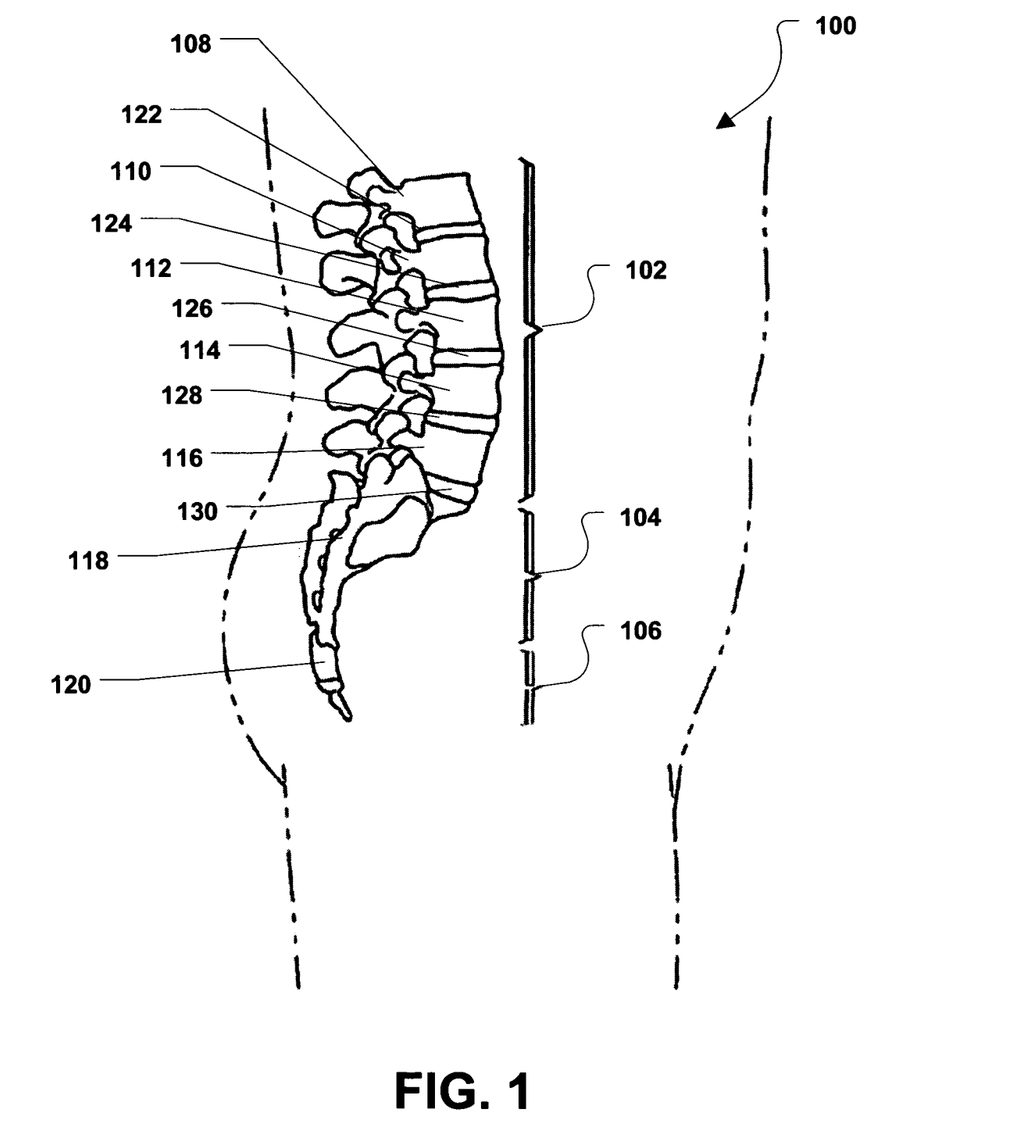
FIG. 1 is a lateral view of a portion of a vertebral column.

Referring initially to FIG. 1, a portion of a vertebral column, designated 100, is shown. As depicted, the vertebral column 100 includes a lumbar region 102, a sacral region 104, and a coccygeal region 106. As is known in the art, the vertebral column 100 also includes a cervical region and a thoracic region. For clarity and ease of discussion, the cervical region and the thoracic region are not illustrated.

As shown in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, damaged, or otherwise in need of repair, augmentation or treatment, that intervertebral lumbar disc 122, 124, 126, 128, 130 can be treated in accordance with one or more of the embodiments described herein.

Figure 2:
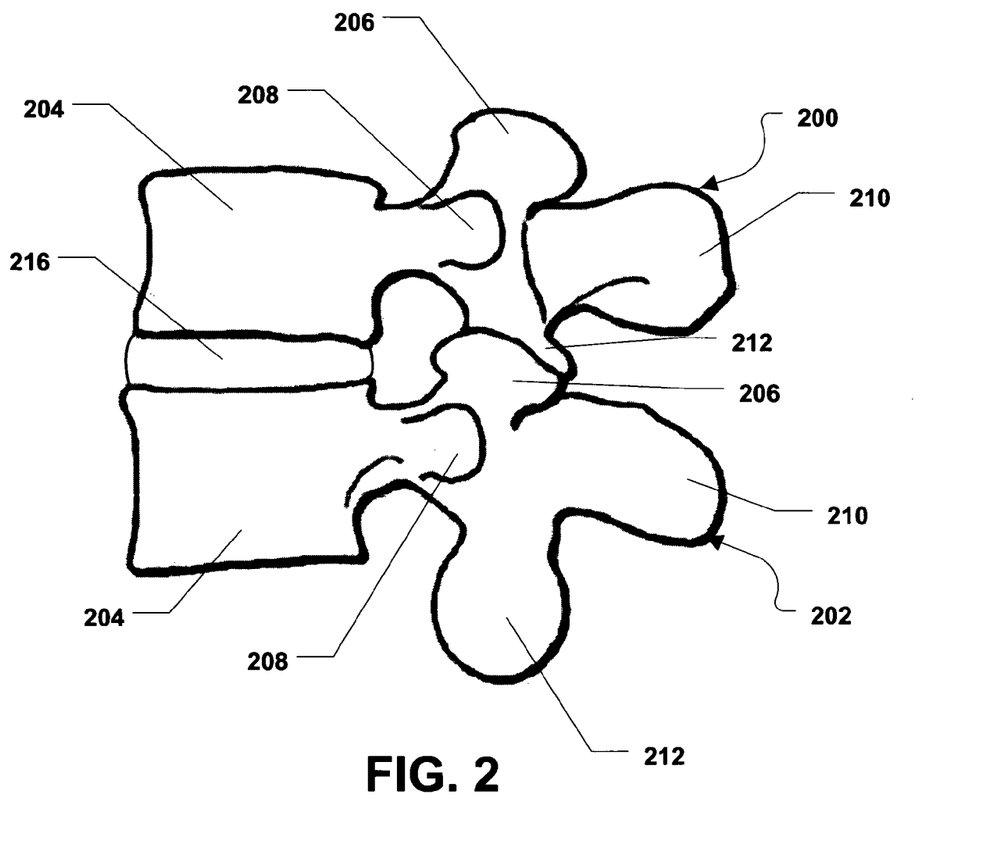
FIG. 2 is a lateral view of a pair of adjacent vertebrae.

FIG. 2 depicts a detailed lateral view of two adjacent vertebrae, e.g., two of the lumbar vertebra 108, 110, 112, 114, 116 shown in FIG. 1. FIG. 2 illustrates a superior vertebra 200 and an inferior vertebra 202. As shown, each vertebra 200, 202 includes a vertebral body 204, a superior articular process 206, a transverse process 208, a spinous process 210 and an inferior articular process 212. FIG. 2 further depicts an intervertebral disc 216 between the superior vertebra 200 and the inferior vertebra 202.

Figure 3:
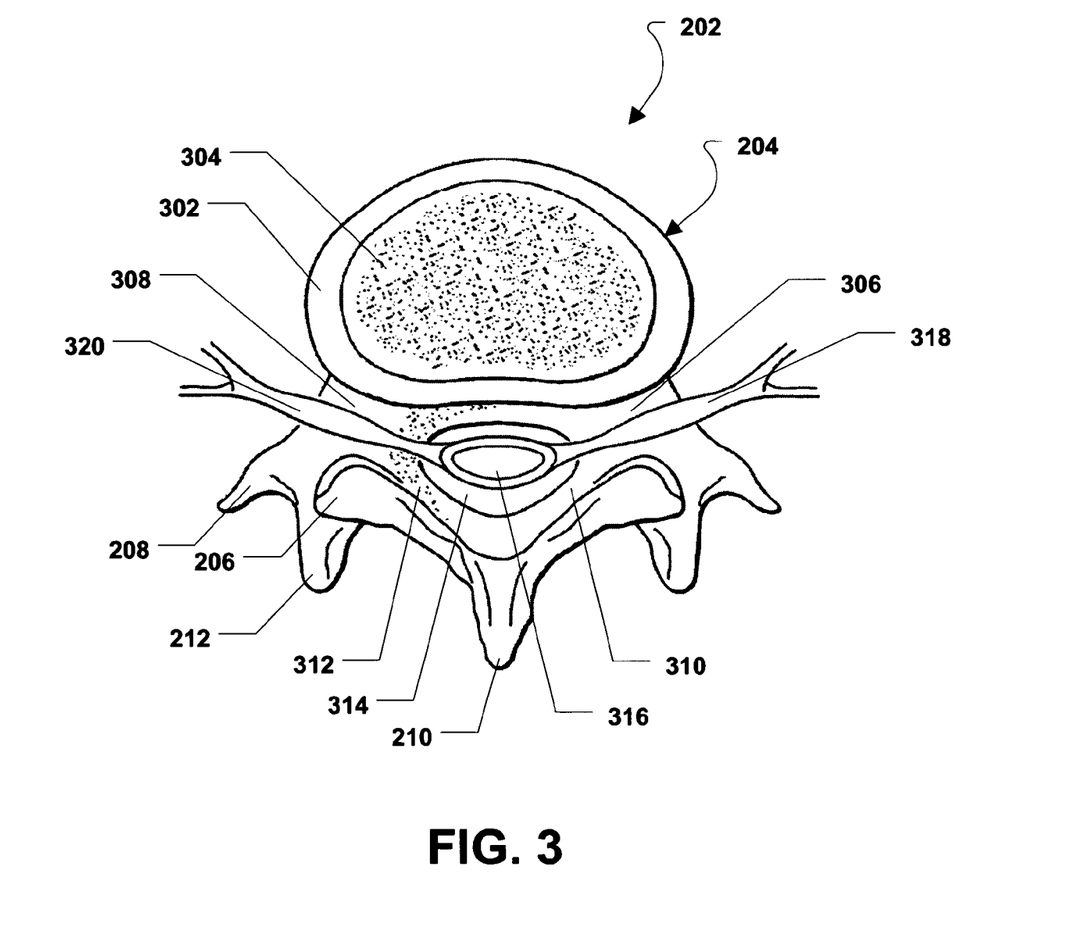
FIG. 3 is a top plan view of a vertebra.

Referring to FIG. 3, a vertebra, e.g., the inferior vertebra 202 (FIG. 2), is illustrated. As shown, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

It is well known in the art that the vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Figure 4:
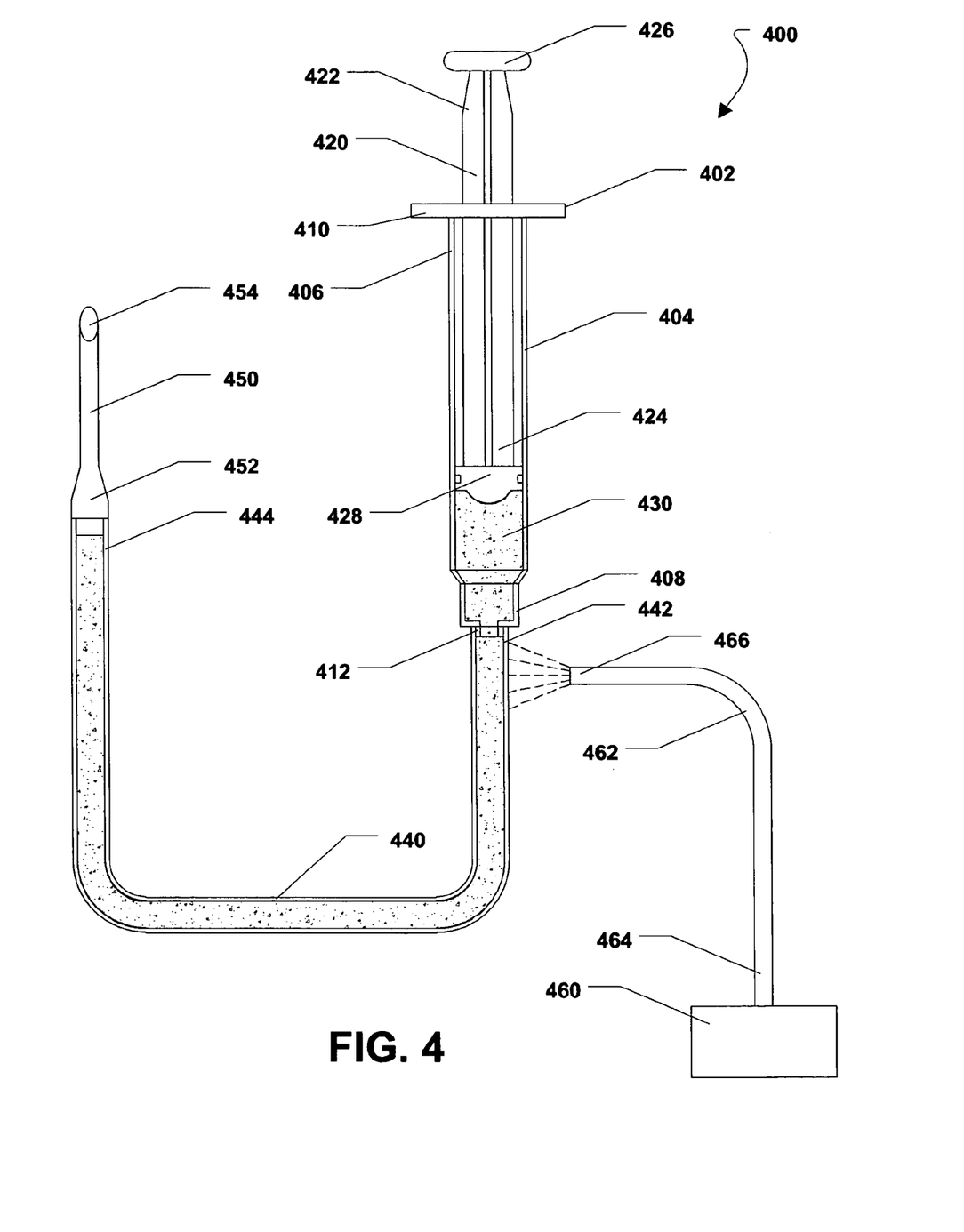
FIG. 4 is a plan view of a first embodiment of an injectable biocompatible material delivery system.

Description of a First Embodiment of an Injectable Biocompatible Material Delivery System Referring to FIG. 4, a first embodiment of an injectable biocompatible material delivery system is shown and is generally designated 400. As illustrated, the system 400 can include an injector, such as a syringe 402. The syringe 402 can include a barrel 404 that can define a proximal end 406 and a distal end 408. The proximal end 406 of the syringe 402 can include a barrel handle 410. Further, the distal end 408 of the syringe 402 can include a needle hilt 412.

As shown in FIG. 4, a plunger 420 can be disposed within the barrel 404 of the syringe. The plunger 420 can include a proximal end 422 and a distal end 424. Also, the proximal end 422 of the plunger 420 can include a plunger handle 426 coupled thereto. Moreover, the distal end 424 of the plunger 420 can include a plunger tip 428. FIG. 4 also indicates that the syringe 400 can be filled with an injectable biocompatible material 430.

In a particular embodiment, the injectable biocompatible material 430 can include any biocompatible material that can undergo transformation from a flowable state to a non-flowable state after activation and curing. Further, the injectable biocompatible material 430 can include one or more polymer materials. For example, the polymer materials can include polyurethane, silicone, silicone polyurethane copolymers, polymethylmethacrylate, epoxy, cyanoacrylate, or a combination thereof.

In a particular embodiment, a material delivery cannula 440 can be placed in fluid communication with, or otherwise connected, to the needle hilt 412 of the syringe 402. In exemplary embodiments, the material delivery cannula 440 can be fastened, coupled, or integrally formed with the needle hilt 412. The material delivery cannula 440 can include a proximal end 442 and a distal end 444. As shown, the proximal end 442 of the material delivery cannula 440 can be connected to the needle hilt 412 of the syringe 402. Further, a material delivery trocar 450 can be coupled to the distal end 444 of the material delivery cannula 440. The material delivery trocar 450 can include a proximal end 452 and a distal end 454 and the proximal end 452 of the material delivery trocar 450 can be coupled, or otherwise connected, to the distal end 444 of the material delivery cannula 440. In a particular embodiment, a material delivery channel can be established within the system 400 by the syringe 402, the material delivery cannula 440, and the material delivery trocar 450.

FIG. 4 further shows that the system 400 can include an energy source, such as a light source 460. In a particular embodiment, the light source 460 can be an ultraviolet (UV) light source, an infrared (IR) light source, another light source, or a combination thereof. As depicted in FIG. 4, a fiber optic cable 462 or other energy transporting member can be connected to the light source 460. The fiber optic cable 462 can include a proximal end 464 and a distal end 466. In a particular embodiment, the proximal end 464 of the fiber optic cable 462 can be connected to the light source 460. Moreover, the distal end 466 of the fiber optic cable 462 can be placed substantially near the proximal end 442 of the material delivery cannula 440 such that the light source 460 is in optical communication with the proximal end 442 of the material delivery cannula 440. The light source 460 can emit light into the fiber optic cable 462, e.g., into the proximal end 464 thereof. The light can travel along the length of the fiber optic cable 462 and exit at the distal end 466 of the fiber optic cable 462. Accordingly, the light from the light source 460 can be transmitted from the light source 460 to a location along the material delivery cannula 440, e.g., to the proximal end 442 of the material delivery cannula 440.

In a particular embodiment, when the plunger 420 is depressed, or otherwise slid, into the barrel 404 of the syringe 402, the plunger 420 can pressurize the injectable biocompatible material 430 within the barrel 404. Further, the movement of the plunger 420 into the barrel 404 can force the biocompatible material 430 to move through the material delivery cannula 440 and the material delivery trocar 450 affixed to the material delivery cannula 440. The biocompatible material 430 can exit material delivery trocar 450.

Additionally, the light emitted by the light source 460 can activate the injectable biocompatible material 430 while the injectable biocompatible material 430 moves through the material delivery cannula 440 and begin the curing process of the injectable biocompatible material 430 before it is actually deposited within the patient. As such, after the injectable biocompatible material 430 is deposited within the patient, the in situ curing time of the injectable biocompatible material 430 can be substantially reduced.

Figure 5:
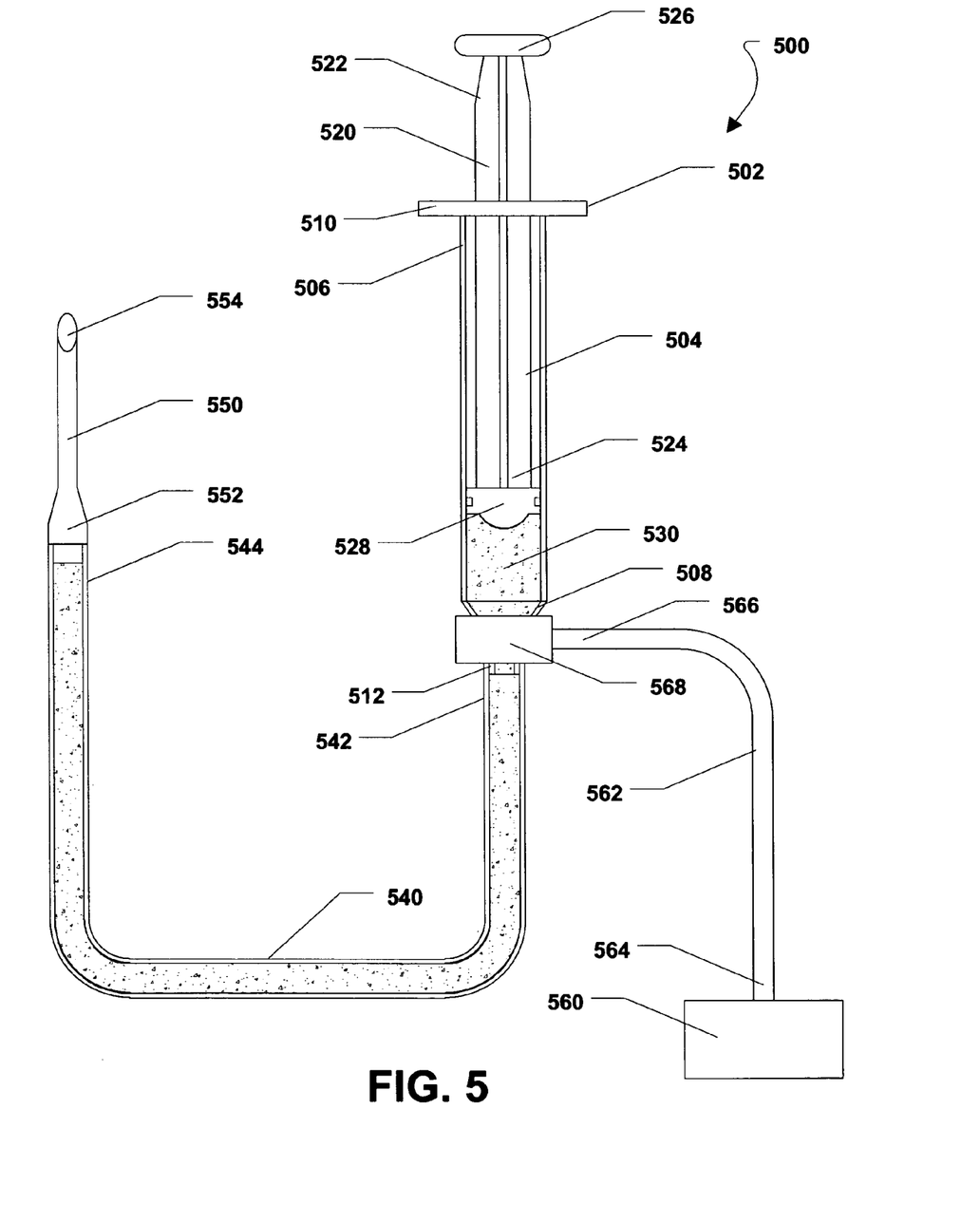
FIG. 5 is a plan view of a second embodiment of an injectable biocompatible material delivery system.

Description of a Second Embodiment of an Injectable Biocompatible Material Delivery System Referring to FIG. 5, a second embodiment of an injectable biocompatible material delivery system is shown and is generally designated 500. As illustrated, the system 500 can include an injector, such as a syringe 502. The syringe 502 can include a barrel 504 that can define a proximal end 506 and a distal end 508. The proximal end 506 of the syringe 502 can include a barrel handle 510. Further, the distal end 508 of the syringe 502 can include a needle hilt 512.

As shown in FIG. 5, a plunger 520 can be disposed within the barrel 504 of the syringe. The plunger 520 can include a proximal end 522 and a distal end 524. Also, the proximal end 522 of the plunger 520 can include a plunger handle 526 coupled thereto. Moreover, the distal end 524 of the plunger 520 can include a plunger tip 528. FIG. 5 also indicates that the syringe 500 can be filled with an injectable biocompatible material 530.

In a particular embodiment, the injectable biocompatible material 530 can include any biocompatible material that can undergo transformation from a flowable state to a non-flowable state after activation and curing. Further, the injectable biocompatible material 530 can include one or more polymer materials. For example, the polymer materials can include polyurethane, silicone, silicone polyurethane copolymers, polymethylmethacrylate, epoxy, cyanoacrylate, or a combination thereof.

In a particular embodiment, a material delivery cannula 540 can be coupled, or otherwise connected, to the needle hilt 512 of the syringe 502. The material delivery cannula 540 can include a proximal end 542 and a distal end 544. As shown, the proximal end 542 of the material delivery cannula 540 can be connected to the needle hilt 512 of the syringe 502. Further, a material delivery trocar 550 can be coupled to the distal end 544 of the material delivery cannula 540. The material delivery trocar 550 can include a proximal end 552 and a distal end 554 and the proximal end 552 of the material delivery trocar 550 can be coupled, or otherwise connected, to the distal end 544 of the material delivery cannula 540. In a particular embodiment, a material delivery channel can be established within the system 500 by the syringe 502, the material delivery cannula 540, and the material delivery trocar 550.

FIG. 5 further shows that the system 500 can include a light source 560. In a particular embodiment, the light source 560 can be an ultraviolet (UV) light source, an infrared (IR) light source, another light source, or a combination thereof. As depicted in FIG. 5, a fiber optic cable 562 can be connected to the light source 560. The fiber optic cable 562 can include a proximal end 564 and a distal end 566. In a particular embodiment, the proximal end 564 of the fiber optic cable 562 can be connected to the light source 560. Moreover, a curing head 568 can be coupled to the distal end 566 of the fiber optic cable 562. As shown, the curing head 568 can circumscribe the distal end 508 of the barrel 504 of the syringe 502. Further, in a particular embodiment, the curing head 568 can be incorporated into, or integrally formed with, the distal end 508 of the barrel 504 of the syringe 502.

The light source 560 can emit light into the fiber optic cable 562, e.g., into the proximal end 564 thereof. The light can travel along the length of the fiber optic cable 562 and exit at the curing head 568 coupled to the distal end 566 of the fiber optic cable 562. In exemplary embodiments, the curing head 568 can include various components (not shown), such as one or more highly reflective surfaces, one or more fiber optic cables, or a combination thereof. The components of the curing head 568 can be configured to transmit light from the light source 560 radially into the syringe 502. Accordingly, the light from the light source 560 can be transmitted from the light source 560 to a location along the syringe 502, e.g., to the distal end 508 of the barrel 504 of the syringe 502.

In a particular embodiment, when the plunger 520 is depressed, or otherwise slid, into the barrel 504 of the syringe 502, the plunger 520 can pressurize the injectable biocompatible material 530 within the barrel 504. Further, the movement of the plunger 520 into the barrel 504 can force the biocompatible material 530 to move through the material delivery cannula 540 and the material delivery trocar 550 affixed to the material delivery cannula 540. The biocompatible material 530 can exit material delivery trocar 550.

Additionally, the light emitted by the light source 560 can activate the injectable biocompatible material 530 just before the injectable biocompatible material 530 exits the syringe 502 and enters the material delivery cannula 540. As such, the injectable biocompatible material 530 can begin curing within the material delivery cannula 540 before the injectable biocompatible material 530 is deposited within a patient. As such, after the injectable biocompatible material 530 is deposited within the patient, the in situ curing time of the injectable biocompatible material 530 can be substantially reduced.

Figure 6:
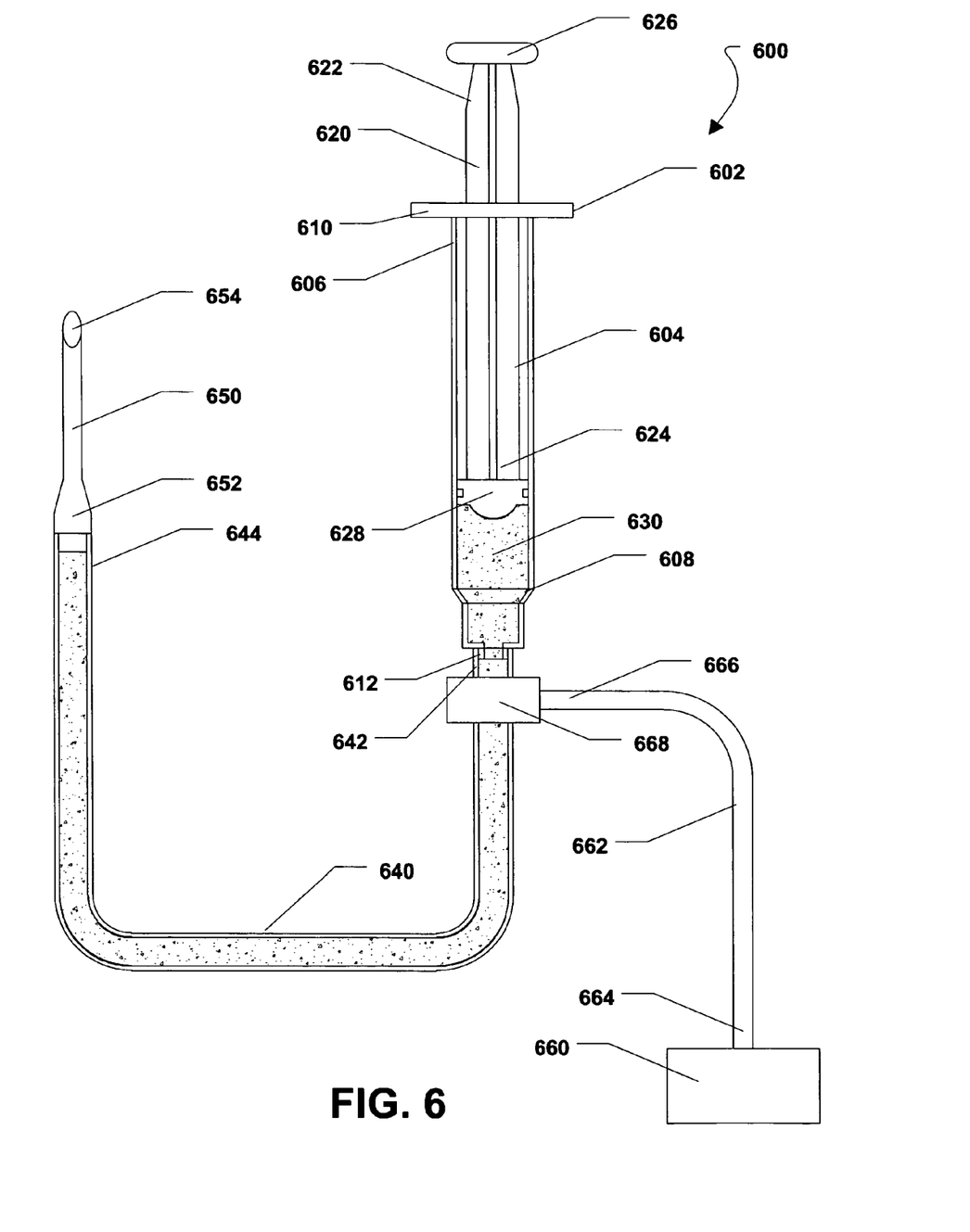
FIG. 6 is a plan view of a third embodiment of an injectable biocompatible material delivery system.

Description of a Third Embodiment of an Injectable Biocompatible Material Delivery System Referring to FIG. 6, a third embodiment of an injectable biocompatible material delivery system is shown and is generally designated 600. As illustrated, the system 600 can include an injector, such as a syringe 602. The syringe 602 can include a barrel 604 that can define a proximal end 606 and a distal end 608. The proximal end 606 of the syringe 602 can include a barrel handle 610. Further, the distal end 608 of the syringe 602 can include a needle hilt 612.

As shown in FIG. 6, a plunger 620 can be disposed within the barrel 604 of the syringe. The plunger 620 can include a proximal end 622 and a distal end 624. Also, the proximal end 622 of the plunger 620 can include a plunger handle 626 coupled thereto. Moreover, the distal end 624 of the plunger 620 can include a plunger tip 628. FIG. 6 also indicates that the syringe 600 can be filled with an injectable biocompatible material 630.

In a particular embodiment, the injectable biocompatible material 630 can include any biocompatible material that can undergo transformation from a flowable state to a non-flowable state after activation and curing. Further, the injectable biocompatible material 630 can include one or more polymer materials. For example, the polymer materials can include polyurethane, silicone, silicone polyurethane copolymers, polymethylmethacrylate, epoxy, cyanoacrylate, or a combination thereof.

In a particular embodiment, a material delivery cannula 640 can be coupled, or otherwise connected, to the needle hilt 612 of the syringe 602. The material delivery cannula 640 can include a proximal end 642 and a distal end 644. As shown, the proximal end 642 of the material delivery cannula 640 can be connected to the needle hilt 612 of the syringe 602. Further, a material delivery trocar 650 can be coupled to the distal end 644 of the material delivery cannula 640. The material delivery trocar 650 can include a proximal end 652 and a distal end 654 and the proximal end 652 of the material delivery trocar 650 can be coupled, or otherwise connected, to the distal end 644 of the material delivery cannula 640. In a particular embodiment, a material delivery channel can be established within the system 600 by the syringe 602, the material delivery cannula 640, and the material delivery trocar 650.

FIG. 6 further shows that the system 600 can include a light source 660. In a particular embodiment, the light source 660 can be an ultraviolet (UV) light source, an infrared (IR) light source, another light source, or a combination thereof. As depicted in FIG. 6, a fiber optic cable 662 can be connected to the light source 660. The fiber optic cable 662 can include a proximal end 664 and a distal end 666. In a particular embodiment, the proximal end 664 of the fiber optic cable 662 can be connected to the light source 660. Moreover, a curing head 668 can be coupled to the distal end 666 of the fiber optic cable 662. As shown, the curing head 668 can circumscribe the proximal end 642 of the material delivery cannula 640. Further, in a particular embodiment, the curing head 668 can be incorporated into, or integrally formed with, the proximal end 642 of the material delivery cannula 640.

The light source 660 can emit light into the fiber optic cable 662, e.g., into the proximal end 664 thereof. The light can travel along the length of the fiber optic cable 662 and exit at the curing head 668 coupled to the distal end 666 of the fiber optic cable 662. The curing head 668 can be configured to transmit light from the light source 660 radially into the material delivery cannula 640. Accordingly, the light from the light source 660 can be transmitted from the light source 660 to a location along the material delivery cannula 640, e.g., to the proximal end 642 of the material delivery cannula 640.

In a particular embodiment, when the plunger 620 is depressed, or otherwise slid, into the barrel 604 of the syringe 602, the plunger 620 can pressurize the injectable biocompatible material 630 within the barrel 604. Further, the movement of the plunger 620 into the barrel 604 can force the biocompatible material 630 to move through the material delivery cannula 640 and the material delivery trocar 650 affixed to the material delivery cannula 640. The biocompatible material 630 can exit material delivery trocar 650.

Additionally, the light emitted by the light source 660 can activate the injectable biocompatible material 630 as the injectable biocompatible material 630 exits the syringe 602 and enters the material delivery cannula 640. As such, the injectable biocompatible material 630 can begin curing within the material delivery cannula 640 before the injectable biocompatible material 630 is deposited within a patient. As such, after the injectable biocompatible material 630 is deposited within the patient, the in situ curing time of the injectable biocompatible material 630 can be substantially reduced.

Figure 7:
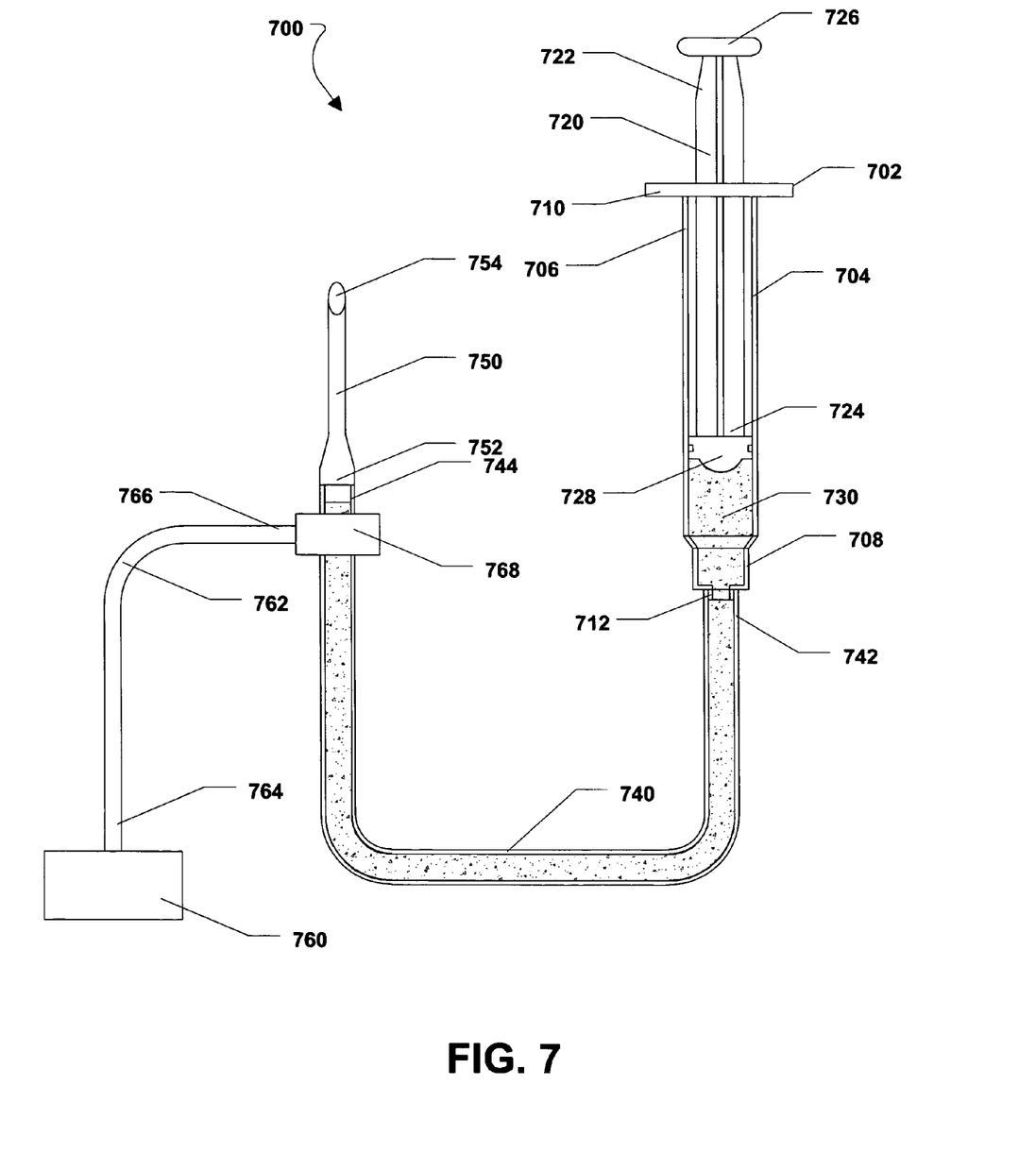
FIG. 7 is a plan view of a fourth embodiment of an injectable biocompatible material delivery system.

Description of a Fourth Embodiment of an Injectable Biocompatible Material Delivery System Referring to FIG. 7, a fourth embodiment of an injectable biocompatible material delivery system is shown and is generally designated 700. As illustrated, the system 700 can include an injector, such as a syringe 702. The syringe 702 can include a barrel 704 that can define a proximal end 706 and a distal end 708. The proximal end 706 of the syringe 702 can include a barrel handle 710. Further, the distal end 708 of the syringe 702 can include a needle hilt 712.

As shown in FIG. 7, a plunger 720 can be disposed within the barrel 704 of the syringe. The plunger 720 can include a proximal end 722 and a distal end 724. Also, the proximal end 722 of the plunger 720 can include a plunger handle 726 coupled thereto. Moreover, the distal end 724 of the plunger 720 can include a plunger tip 728. FIG. 7 also indicates that the syringe 700 can be filled with an injectable biocompatible material 730.

In a particular embodiment, the injectable biocompatible material 730 can include any biocompatible material that can undergo transformation from a flowable state to a non-flowable state after activation and curing. Further, the injectable biocompatible material 730 can include one or more polymer materials. For example, the polymer materials can include polyurethane, silicone, silicone polyurethane copolymers, polymethylmethacrylate, epoxy, cyanoacrylate, or a combination thereof.

In a particular embodiment, a material delivery cannula 740 can be coupled, or otherwise connected, to the needle hilt 712 of the syringe 702. The material delivery cannula 740 can include a proximal end 742 and a distal end 744. As shown, the proximal end 742 of the material delivery cannula 740 can be connected to the needle hilt 712 of the syringe 702. Further, a material delivery trocar 750 can be coupled to the distal end 744 of the material delivery cannula 740. The material delivery trocar 750 can include a proximal end 752 and a distal end 754 and the proximal end 752 of the material delivery trocar 750 can be coupled, or otherwise connected, to the distal end 744 of the material delivery cannula 740. In a particular embodiment, a material delivery channel can be established within the system 700 by the syringe 702, the material delivery cannula 740, and the material delivery trocar 750.

FIG. 7 further shows that the system 700 can include a light source 760. In a particular embodiment, the light source 760 can be an ultraviolet (UV) light source, an infrared (IR) light source, another light source, or a combination thereof. As depicted in FIG. 7, a fiber optic cable 762 can be connected to the light source 760. The fiber optic cable 762 can include a proximal end 764 and a distal end 766. In a particular embodiment, the proximal end 764 of the fiber optic cable 762 can be connected to the light source 760. Moreover, a curing head 768 can be coupled to the distal end 766 of the fiber optic cable 762. As shown, the curing head 768 can circumscribe the distal end 744 of the material delivery cannula 740. Further, in a particular embodiment, the curing head 768 can be incorporated into, or integrally formed with, the distal end 744 of the material delivery cannula 740.

The light source 760 can emit light into the fiber optic cable 762, e.g., into the proximal end 764 thereof. The light can travel along the length of the fiber optic cable 762 and exit at the curing head 768 coupled to the distal end 766 of the fiber optic cable 762. The curing head 768 can be configured to transmit light from the light source 760 radially into the material delivery cannula 740. Accordingly, the light from the light source 760 can be transmitted from the light source 760 to a location along the material delivery cannula 740, e.g., to the distal end 744 of the material delivery cannula 740.

In a particular embodiment, when the plunger 720 is depressed, or otherwise slid, into the barrel 704 of the syringe 702, the plunger 720 can pressurize the injectable biocompatible material 730 within the barrel 704. Further, the movement of the plunger 720 into the barrel 704 can force the biocompatible material 730 to move through the material delivery cannula 740 and the material delivery trocar 750 affixed to the material delivery cannula 740. The biocompatible material 730 can exit material delivery trocar 750.

Additionally, the light emitted by the light source 760 can activate the injectable biocompatible material 730 as the injectable biocompatible material 730 exits the syringe 702 and enters the material delivery cannula 740. As such, the injectable biocompatible material 730 can begin curing within the material delivery cannula 740 before the injectable biocompatible material 730 is deposited within a patient. As such, after the injectable biocompatible material 730 is deposited within the patient, the in situ curing time of the injectable biocompatible material 730 can be substantially reduced.

Figure 8:
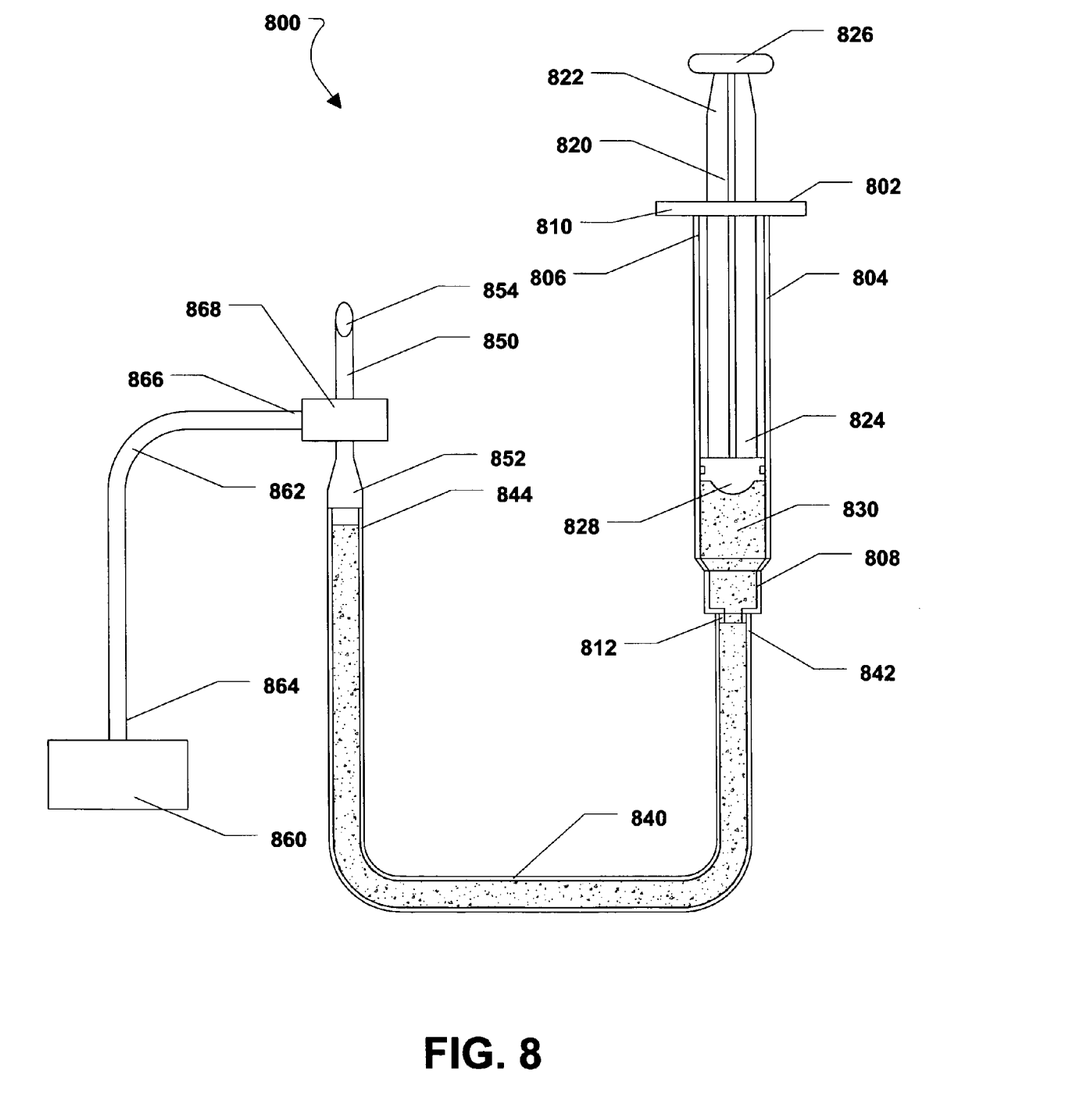
FIG. 8 is a plan view of a fifth embodiment of an injectable biocompatible material delivery system.

Description of a Fifth Embodiment of an Injectable Biocompatible Material Delivery System Referring to FIG. 8, a fifth embodiment of an injectable biocompatible material delivery system is shown and is generally designated 800. As illustrated, the system 800 can include an injector, such as a syringe 802. The syringe 802 can include a barrel 804 that can define a proximal end 806 and a distal end 808. The proximal end 806 of the syringe 802 can include a barrel handle 810. Further, the distal end 808 of the syringe 802 can include a needle hilt 812.

As shown in FIG. 8, a plunger 820 can be disposed within the barrel 804 of the syringe. The plunger 820 can include a proximal end 822 and a distal end 824. Also, the proximal end 822 of the plunger 820 can include a plunger handle 826 coupled thereto. Moreover, the distal end 824 of the plunger 820 can include a plunger tip 828. FIG. 8 also indicates that the syringe 800 can be filled with an injectable biocompatible material 830.

In a particular embodiment, the injectable biocompatible material 830 can include any biocompatible material that can undergo transformation from a flowable state to a non-flowable state after activation and curing. Further, the injectable biocompatible material 830 can include one or more polymer materials. For example, the polymer materials can include polyurethane, silicone, silicone polyurethane copolymers, polymethylmethacrylate, epoxy, cyanoacrylate, or a combination thereof.

In a particular embodiment, a material delivery cannula 840 can be coupled, or otherwise connected, to the needle hilt 812 of the syringe 802. The material delivery cannula 840 can include a proximal end 842 and a distal end 844. As shown, the proximal end 842 of the material delivery cannula 840 can be connected to the needle hilt 812 of the syringe 802. Further, a material delivery trocar 850 can be coupled to the distal end 844 of the material delivery cannula 840. The material delivery trocar 850 can include a proximal end 852 and a distal end 854 and the proximal end 852 of the material delivery trocar 850 can be coupled, or otherwise connected, to the distal end 844 of the material delivery cannula 840. In a particular embodiment, a material delivery channel can be established within the system 800 by the syringe 802, the material delivery cannula 840, and the material delivery trocar 850.

FIG. 8 further shows that the system 800 can include a light source 860. In a particular embodiment, the light source 860 can be an ultraviolet (UV) light source, an infrared (IR) light source, another light source, or a combination thereof. As depicted in FIG. 8, a fiber optic cable 862 can be connected to the light source 860. The fiber optic cable 862 can include a proximal end 864 and a distal end 866. In a particular embodiment, the proximal end 864 of the fiber optic cable 862 can be connected to the light source 860. Moreover, a curing head 868 can be coupled to the distal end 866 of the fiber optic cable 862. As shown, the curing head 868 can circumscribe the material delivery trocar 850 near the proximal end 852 of the material delivery trocar 850. Further, in a particular embodiment, the curing head 868 can be incorporated into, or integrally formed with, the material delivery trocar 850.

The light source 860 can emit light into the fiber optic cable 862, e.g., into the proximal end 864 thereof. The light can travel along the length of the fiber optic cable 862 and exit at the curing head 868 coupled to the distal end 866 of the fiber optic cable 862. The curing head 868 can be configured to transmit light from the light source 860 radially into the material delivery trocar 850. Accordingly, the light from the light source 860 can be transmitted from the light source 860 to a location along the material delivery trocar 850, e.g., near the proximal end 852 of the material delivery trocar 850.

In a particular embodiment, when the plunger 820 is depressed, or otherwise slid, into the barrel 804 of the syringe 802, the plunger 820 can pressurize the injectable biocompatible material 830 within the barrel 804. Further, the movement of the plunger 820 into the barrel 804 can force the biocompatible material 830 to move through the material delivery cannula 840 and the material delivery trocar 850 affixed to the material delivery cannula 840. The biocompatible material 830 can exit the system 800 via the material delivery trocar 850.

Additionally, the light emitted by the light source 860 can activate the injectable biocompatible material 830 as the injectable biocompatible material 830 exits the material delivery cannula 840 and enters the material delivery trocar 850. As such, the injectable biocompatible material 830 can begin curing within the material delivery trocar 850 before the injectable biocompatible material 830 is deposited within a patient. As such, after the injectable biocompatible material 830 is deposited within the patient, the in situ curing time of the injectable biocompatible material 830 can be substantially reduced.

Figure 9:
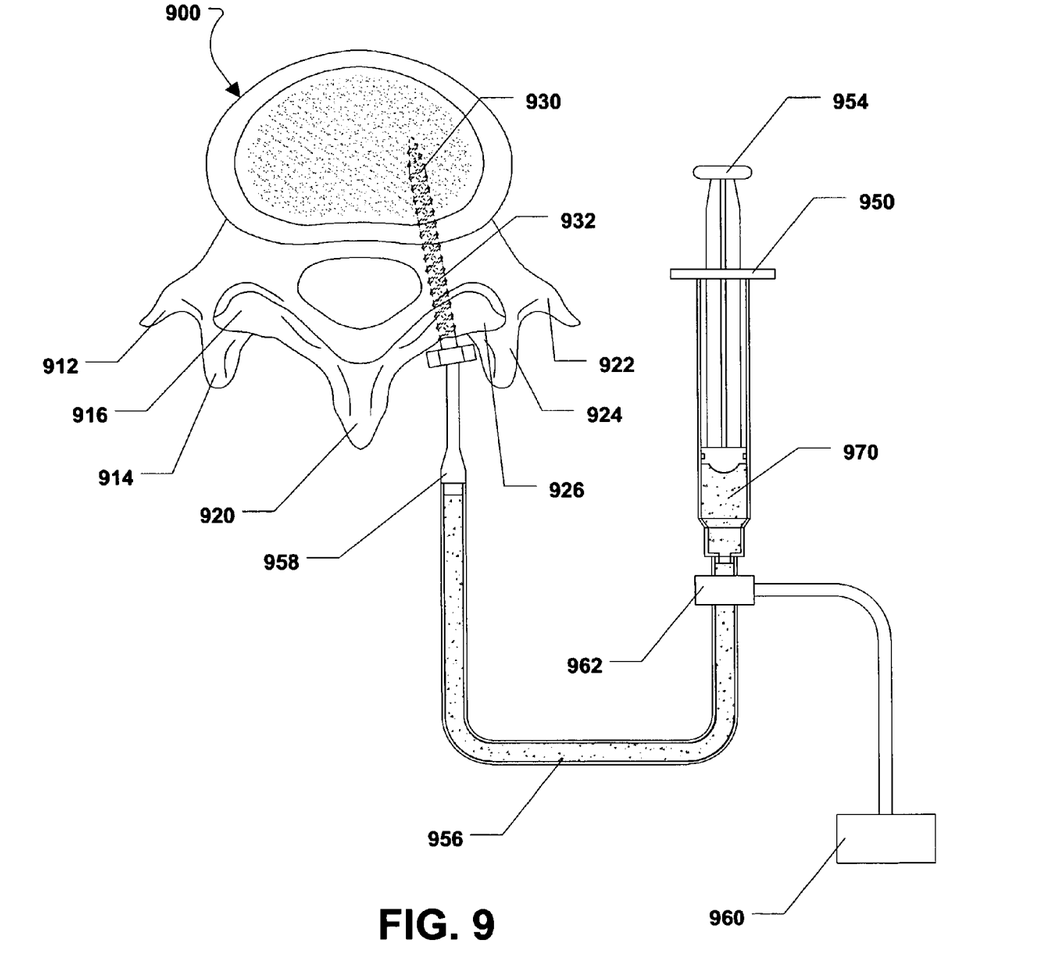
FIG. 9 is a plan view of an embodiment of an injectable biocompatible material delivery system engaged with a fenestrated bone screw installed in a vertebra.

Description of an Injectable Biocompatible Material Delivery System Engaged with a Fenestrated Bone Screw Installed in a Vertebra Referring to FIG. 9, a vertebra is shown and is generally designated 900. The vertebra 900 can include a vertebral body 910, a first transverse process 912, a first inferior articular process 914, and a first superior articular process 916. Further, the vertebra 900 can include a spinous process 920, a second transverse process 922, a second inferior articular process 924, and a second superior articular process 926.

As shown, a bone screw 930 can be installed within the vertebra 900. For example, the bone screw 930 can be installed in the vertebra 900 near the second transverse process 922 above the second inferior articular process 924 and below the second superior articular process 926. In a particular embodiment, the bone screw 930 can be hollow and can include a plurality of fenestrations 932.

As shown in FIG. 9, an injectable biocompatible material delivery system 950 can be coupled to the bone screw 930. The injectable biocompatible material delivery system 950 can be an injectable biocompatible material delivery system according to one or more of the embodiments described herein.

For example, the injectable biocompatible material delivery system 950 can include a syringe 952 having a plunger 954. A material delivery cannula 956 can be connected to the syringe 952 and a material delivery trocar 958 can be connected to the material delivery cannula 956. The material delivery trocar 958 can also be connected to the bone screw 930. FIG. 9 shows that the injectable biocompatible material delivery system 950 can also include a light source 960 having a curing head 962 that can circumscribe the material delivery cannula 954.

In a particular embodiment, the injectable biocompatible material delivery system 950 can be used to delivery an injectable biocompatible material 970 to an area surrounding the bone screw 930 via the fenestrations 932 in the bone screw 930. For example, the plunger 954 can be moved into the syringe 952 in order to pressurize the injectable biocompatible material 970 and cause the injectable biocompatible material 970 to exit the syringe 952 and move through the material delivery cannula 954 and the material delivery trocar 958. As the injectable biocompatible material 970 moves through the material delivery cannula 956, the injectable biocompatible material 970 can pass through the curing head 962. The curing head 962 can transmit light from the light source 960 directly into the injectable biocompatible material 970. Further, the light can activate the injectable biocompatible material 970 and the activated injectable biocompatible material can begin to cure within the material delivery cannula 956.

Accordingly, the activated injectable biocompatible material 970 can be curing as the activated injectable biocompatible material 970 exits the bone screw 930 and is deposited in the vertebra 900. Further, an in situ curing time of the injectable biocompatible material 970 can be substantially reduced by activating the injectable biocompatible material 970 within the injectable biocompatible material delivery system 950 as the injectable biocompatible material 970 moves through the injectable biocompatible material delivery system 950.

Depending on a location of the curing head 962, the in situ curing time can vary. For example, an in situ curing time associated with placing the curing head 962 as shown, e.g., at or near the interface between the syringe 950 and the material delivery cannula 956, can be relatively shorter than an in situ curing time associated with placing the curing head 962 at or near the interface between the material delivery cannula 956 and the material delivery trocar 958. The location of the curing head can be selected based at least in part on the identity of the injectable biocompatible material and the flow characteristics of the injectable biocompatible material after activation. Further, although the delivery system is illustrated in FIG. 9 in combination with a fenestrated bone screw, the system can be utilized to deliver injectable biocompatible material directly to a fracture site or other point of use without utilizing a fenestrated screw. For example, the system can be utilized to deliver injectable biocompatible material to a nucleus of an intervertebral disc in order to replace or augment nucleus pulposus material.

Description of a Method of Treating a Spine

Figure 10:
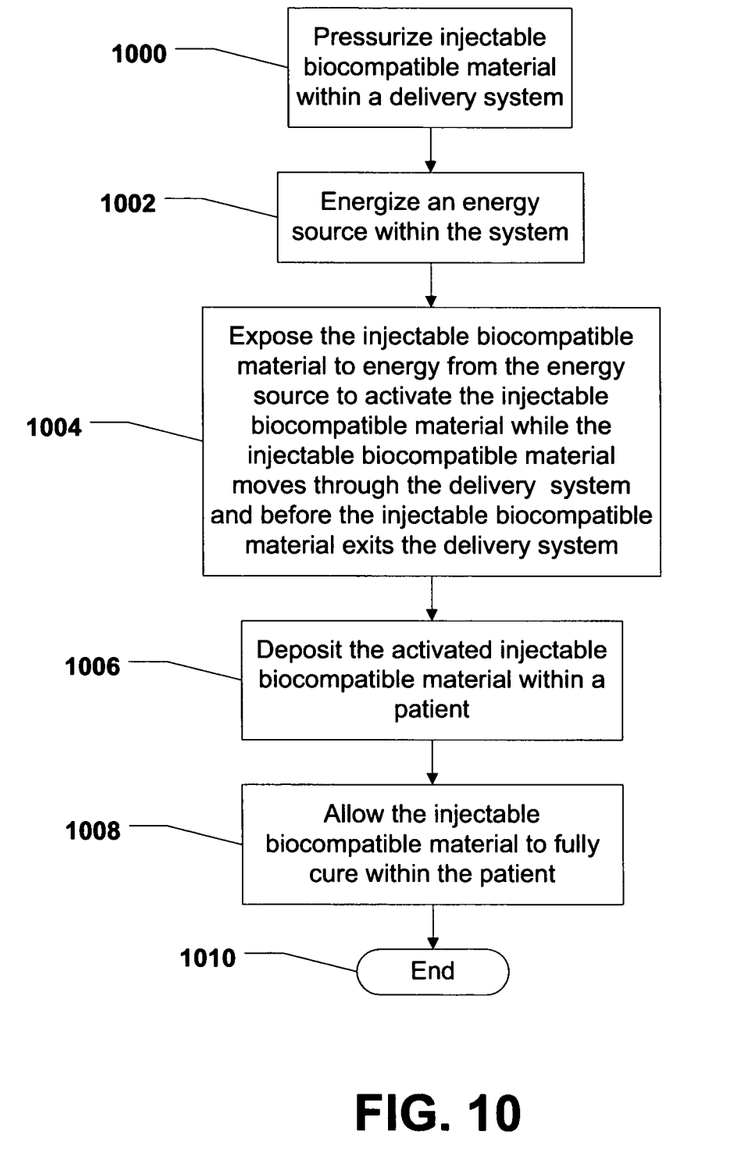
FIG. 10 is a flow chart illustrating a method of delivering an injectable biocompatible material.

Referring to FIG. 10, a method of treating a spine is shown and commences at block 1000. At block 1000, an injectable biocompatible material is pressurized within a delivery system. In a particular embodiment, the injectable biocompatible material can be pressurized by depressing a plunger within a syringe. At block 1002, an energy source within the system is energized. For example, the energy source can be a UV light source or an IR light source. Alternatively, the energy source can be a heat source or another energy source.

Proceeding to block 1004, the injectable biocompatible material can be exposed to curing energy from the energy source in order to activate the injectable biocompatible material while the injectable biocompatible material moves through the delivery system. Further, the injectable biocompatible material can be activated before the injectable biocompatible material exits the delivery system. At block 1006, the activated injectable biocompatible material can be deposited within a patient. Thereafter, at block 1008, the activated injectable biocompatible material is allowed to fully cure in situ within the patient. The method can end at state 1010.

In a particular embodiment, the injectable biocompatible material can be used in conjunction with a bone screw, e.g., a fenestrated bone screw, in order to treat a vertebral fracture, such as a process fracture. Further, the injectable biocompatible material can be used to treat a vertebral compression fracture. The injectable biocompatible material can also be used to bond facet joints or to glue other boney tissue. Moreover, the injectable biocompatible material can be used to anchor spinal implants, knee implants, hip implants, shoulder implants, or other implants. Also, the injectable biocompatible material can be used to replace or augment nucleus pulposus material.

CONCLUSION

With the configuration of structure described above, the injectable biocompatible material delivery system according to one or more of the embodiments herein provides a device that can be used to deliver an injectable biocompatible material to a patient. For example, the injectable biocompatible material can be delivered to one or more bones along a spine of a patient. Also, the injectable biocompatible material can be delivered to an intervertebral disc within a patient. Accordingly, the injectable biocompatible material delivery system can be used to treat a spine and substantially alleviate or minimize one or more symptoms associated with disc degeneration, facet joint degeneration, or a combination thereof.

During delivery of the injectable biocompatible material, a light source along the system can activate the injectable biocompatible material so that the injectable biocompatible material can begin curing within the system prior to delivery within the patient. As such, the in situ curing time of the injectable biocompatible material can be substantially reduced. In a particular embodiment, the in situ curing time can be based on the type of injectable biocompatible material and the location within the system at which curing of the injectable biocompatible material is activated. For example, the earlier the injectable biocompatible material is activated within the system the shorter the in situ curing time will be for a particular injectable biocompatible material.

In each of the systems described herein, the syringe, the material delivery cannula, the material delivery trocar, or a combination thereof can be transparent or translucent in order to facilitate the transmission of light energy into the injectable biocompatible material. Additionally, in the event an alternative energy source is incorporated into the system, e.g., a heat source, the syringe, the material delivery cannula, the material delivery trocar, or a combination thereof can be thermally conductive in order to facilitate the transmission of heat energy into the injectable biocompatible material.

Also, the injectable biocompatible material can be a single component material or a multiple component material prior to implantation and curing. After implantation and curing, the injectable biocompatible material can be biostable, bioresorbable, or a combination thereof.

In one or more alternative embodiments, the injectable biocompatible material delivery system can be used to deliver an injectable biocompatible material to one or more other bones within a patient. Further, the injectable biocompatible material delivery system can be used to deliver an injectable biocompatible material to other tissue, e.g., soft tissue, within a patient. For example, the injectable biocompatible material can be deposited directly within a disc space, a facet capsule, a vertebral body, or within other soft tissues near a patient's spinal column.

In one or more other alternative embodiments, the injectable biocompatible material can be deposited within a containment device such as a balloon, a woven bag, an expandable cage, or other similar containment device. Depositing the injectable biocompatible material in a containment device can form a complete nucleus implant, a partial nucleus implant, a disc prostheses, a fusion case, an intervertebral spacer, a vertebral augmentation implant, a spinal rod, an interspinous spacer, a facet cushioning layer, or another similar device.

Further, in one or more alternative embodiments, the injector within the system can be any type of injector that can pressurize the injectable biocompatible material within the system. For example, the plunger within the injector can be threaded and as the plunger is rotated it advances within the injector and pressurizes the injectable biocompatible material. Also, the injector can be configured similar to a caulk gun and as a handle on the injector is squeezed the plunger can advance within the injector and pressurize the injectable biocompatible material. Further, the plunger within the injector can be electrically driven or pneumatically driven.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An injectable biocompatible material delivery system, comprising:
    an injector including an inner surface defining a chamber having an injectable biocompatible material disposed therein, the injector including a needle hilt at a distal end thereof;
    a plunger movably disposed in the chamber configured to push the injectable biocompatible material through the chamber, the plunger having an outer surface that forms a friction fit with the inner surface of the injector to maintain the plunger in the chamber;
    a material delivery cannula in fluid communication with the chamber including a proximal end connected to the needle hilt of the injector;
    a material delivery trocar in fluid communication with the material delivery cannula, the material delivery trocar having a proximal end engaged to the material delivery cannula and a beveled distal end, the proximal end having a greater diameter than the beveled distal end; and
    a light source that emits infrared light to at least a portion of the injector, at least a portion of the material delivery cannula, or a combination thereof, wherein the light source activates the injectable biocompatible material as it moves past the light source and within the system, the light source including a fiber optic cable attached thereto and positioned substantially near the proximal end of the material delivery cannula such that the light source is in optical communication with the proximal end of the material delivery cannula, and
    wherein at least a portion of the injector, at least a portion of the material delivery cannula, or a combination thereof, is translucent or transparent.

2. The system of claim 1, wherein the injectable biocompatible material begins curing before it exits the system.

3. The system of claim 1, further comprising a curing head in optical communication with the light source, wherein the curing head is configured to transmit light to at least a portion of the injector, a portion of the material delivery cannula, or a combination thereof.

4. The system of claim 3, further comprising a fiber optic cable connected between the light source and the curing head.

5. The system of claim 3, wherein the injector includes a syringe having a proximal end and a distal end and wherein the curing head circumscribes the distal end of the syringe.

6. The system of claim 5, wherein the curing head is integrally formed with the distal end of the syringe.

7. The system of claim 3, wherein the material delivery cannula includes a proximal end and a distal end and wherein the curing head circumscribes the proximal end of the material delivery cannula.

8. The system of claim 7, wherein the curing head is integrally formed with the proximal end of the material delivery cannula.

9. The system of claim 3, wherein the material delivery cannula includes a proximal end and a distal end and wherein the curing head circumscribes the distal end of the material delivery cannula.

10. The system of claim 9, wherein the curing head is integrally formed with the distal end of the material delivery cannula.

11. The system of claim 1, wherein the light source is configured to emit light to at least a portion of the syringe, at least a portion of the material delivery cannula, at least a portion of the material delivery trocar, or a combination thereof, and wherein the light source is further configured to activate an injectable biocompatible material as it moves through the system.

12. The system of claim 11, further comprising a curing head in optical communication with the light source wherein the curing head is configured to transmit light to the material delivery trocar.

13. The system of claim 12, further comprising a fiber optic cable connected between the light source and the curing head.

14. The system of claim 12, wherein the material delivery trocar includes a proximal end and a distal end and wherein the curing head circumscribes the proximal end of the material delivery trocar.

15. The system of claim 14, wherein the curing head is integrally formed with the proximal end of the material delivery trocar.

16. The system of claim 1, wherein the injectable biocompatible material is biostable, bioresorbable, or a combination thereof after curing.

17. The system of claim 1, wherein the injectable biocompatible material comprises at least one of polyurethane, silicone, silicone polyurethane, copolymers, polymethylmethacrylate, epoxy, and cyanoacrylate.

18. The system of claim 1, wherein the outer surface of the plunger has an essential absence of threads.

19. An injectable biocompatible material delivery system, comprising:
- an injector including an inner surface defining a chamber having an injectable biocompatible material disposed therein, the injector including a needle hilt at a distal end thereof;
- a plunger movably disposed in the chamber configured to push the injectable biocompatible material through the chamber, the plunger having an outer surface that forms a friction fit with the inner surface of the injector to maintain the plunger in the chamber;
- a material delivery cannula in fluid communication with the chamber of the injector and including a proximal end connected to the needle hilt of the injector;
- a material delivery trocar in fluid communication with the material delivery cannula, the material delivery trocar having a proximal end engaged to the material delivery cannula and a beveled distal end, the proximal end having a greater diameter than the beveled distal end;
- a material delivery channel established within the injector and the material delivery cannula; and
- an energy source that emits curing energy to at least a portion of the material delivery channel to activate the injectable biocompatible material as it moves past the energy source and within the material delivery channel, the energy source including a fiber optic cable attached thereto and positioned substantially near the proximal end of the material delivery cannula such that the energy source is in optical communication with the proximal end of the material delivery cannula, and
wherein at least a portion of the injector, at least a portion of the material delivery cannula, or a combination thereof, is translucent or transparent.

20. An injectable biocompatible material delivery system, comprising:
- a syringe including an inner surface defining a chamber having an injectable biocompatible material disposed therein;
- a plunger movably disposed in the chamber configured to push the injectable biocompatible material through the chamber, the plunger having a distal end that forms a friction fit with the inner surface of the syringe to maintain the plunger in the chamber;
- a material delivery cannula including a proximal end coupled to the syringe and a distal end;
- a material delivery trocar coupled to the distal end of the material delivery cannula, the material delivery trocar having a first end and a beveled second end, the first end having a greater diameter than the beveled second end;
- a material delivery channel established within the syringe, the material delivery cannula, and the material delivery trocar; and
- an energy source configured to emit curing energy to at least a portion of the material delivery channel to activate an injectable biocompatible material as it moves past the energy source and within the material delivery channel, the energy source including a fiber optic cable attached thereto and positioned substantially near the proximal end of the material delivery cannula such that the energy source is in optical communication with the proximal end of the material delivery cannula,
wherein at least a portion of the syringe, at least a portion of the material delivery cannula, at least a portion of the material delivery trocar, or a combination thereof, is translucent or transparent.

* * * * *